(12) United States Patent
Ben Yehuda et al.

(10) Patent No.: US 6,797,302 B1
(45) Date of Patent: Sep. 28, 2004

(54) ENVIRONMENTALLY COMPATIBLE PROCESSES COMPOSITIONS AND MATERIALS TREATED THEREBY

(76) Inventors: Nimrod Ben Yehuda, Kiryat Tivon (IL); Eliahu Margalit, Kibbutz Bror-Chail (IL)

( * ) Notice: Subject to any disclaimer, the term of this patent is extended or adjusted under 35 U.S.C. 154(b) by 0 days.

(21) Appl. No.: 09/744,681
(22) PCT Filed: Jul. 22, 1999
(86) PCT No.: PCT/IL99/00403
§ 371 (c)(1), (2), (4) Date: Jun. 6, 2001
(87) PCT Pub. No.: WO00/05969
PCT Pub. Date: Feb. 10, 2000

(30) Foreign Application Priority Data

Jul. 27, 1998 (IL) .................................................. 125520

(51) Int. Cl.⁷ ............................. A23B 4/12; A23B 4/22; A23B 7/152
(52) U.S. Cl. ........................ 426/335; 426/615; 426/637
(58) Field of Search ................................ 426/335, 615, 426/637

(56) References Cited

U.S. PATENT DOCUMENTS

| 3,506,458 | A | 4/1970 | Martin |
| 3,996,386 | A | 12/1976 | Malkki et al. |
| 4,915,955 | A | 4/1990 | Gömöri |
| 5,085,880 | A | 2/1992 | Devic |
| 5,535,667 | A | 7/1996 | Dalmasso et al. |
| 5,658,595 | A | 8/1997 | Van Os |

FOREIGN PATENT DOCUMENTS

| FR | 2 728 143 A1 | 6/1996 |
| WO | WO 96/18301 A1 | 6/1996 |

OTHER PUBLICATIONS

J. Hajslova and J. Davidek; "Sprout Inhibitors IPC and CIPC in treated potatoes".

Rami Pedahzur, Ovadia Lev, Badri Fattal, and Hillei Shuval; "The Interaction of Silver Ions and Hydrogen Peroxide in the Inactivation of *E. Coli*: A Preliminary Evaluation of a New Long Acting Residual Drinking Water Disinfectant"; 1995.

Hillel Shuval, Badri Fattal, Abid Nassar, Ovadia Lev, and Rami Pedahzur; "The Study of the Synergism Between Oligodynamic Silver and Hydrogen Peroxide as a Long–Acting Water Disingectant"; 1995.

Yada et al. "The Effect of Maleic Hydrazide (Potassium Salt) on Potato Yield, Sugar Contents and Chip Color if Kennebec and Norchip Cultivars", *American Potato*, vol. 68, pp. 705–709, (1991).

Kirk–Othmer, "Hydrogen Peroxide", *Encyclopedia of Chemical Technology* $4^{th}$*Edition*, vol. 13, pp. 961–995.

Afek et al., "New Approaches for Inhibitions of Sprouting and Reduction of Weight Loss During Storage", Abstractions of Conference Papers, Posters & Demonstrations, $13^{th}$ Triennial Conference of the European Association for Potato Research, Jul. 14–19, Veldhoven Netherlands and Postharvest, Taupo, New Zealand, Aug. 1996.

Shuval et al., "The Study of synergism between oligodynamic silver and hydrogen peroxide as a long–acting water disinfectant", *Water Supply*, vol. 13, No. 2, pp. 241–251, (1995).

Clayton et al, "Potato Seed Hygiene: Cleaning, Disinfecting or Both?", Presentation at meeting of European Association for Potato Research, Mar. 25–29, 1998, Aberdeen, Scotland.

Nir et al, *HaSadeh*, 74(12):1326–1327 (1994).

Ora Smith, *Potatoes: Production Storing Processing*, The Avi Publishing Company, Inc. Westport, CT, pp. 34–51, 124–133, 344–351, and 398–399 (1968).

*Primary Examiner*—Helen Pratt
(74) *Attorney, Agent, or Firm*—Browdy and Neimark, P.L.L.C.

(57) ABSTRACT

The present invention relates to environmentally friendly processes and compositions for prevention of qualitative deterioration and quantitative loss of plant matter and foodstuffs, during all stages of storage and handling, including pre- and post-harvest, pre- and post-planting, distribution and marketing. The processes and compositions of the present invention can also be used to prevent sprouting and rooting, and to promote fecundity of certain plant matter. The processes and compositions of the present invention can also be used to eliminate or reduce quantities of harmful organisms and substances from soil, other growth media and substrates, equipment, materials water, workspaces and surfaces.

19 Claims, No Drawings

ENVIRONMENTALLY COMPATIBLE PROCESSES COMPOSITIONS AND MATERIALS TREATED THEREBY

The present application is the national stage under 35 U.S.C. 371 of PCT/IL99/00403, filed Jul. 22, 1999.

FIELD OF THE INVENTION

The present invention concerns environmentally friendly processes and compositions for preventing qualitative deterioration and quantitative loss of plant matter and foodstuffs, during all stages of storage and handling, including pre and post harvest, pre and post planting, distribution and marketing, as well as for preventing sprouting, rooting, and promoting fecundity of certain plant matter. The processes and compositions of the present invention can also be used to reduce and eliminate harmful organisms and substances from earth, other growth media and substrates, equipment, materials, water, spaces and surfaces.

BACKGROUND OF THE INVENTION

The present invention involves processes and compositions utilizing primarily aqueous hydrogen peroxide for preventing qualitative and quantitative loss of foodstuffs and plant matter during storage and/or handling of such foodstuffs and plant matter. The present invention also involves a process for effecting Epical Dominance Breakdown in certain plant propagation material and as a consequence achieving a number of notable benefits, including storage stability of the plant propagation material itself and higher product yields, when such material is planted. The processes and compositions of the present invention can also be used to reduce and eliminate harmful organisms and substances from earth, other growth media and substrates, equipment, materials, water, spaces and surfaces.

Hydrogen peroxide itself is an environmentally friendly material because its decomposition products are water and oxygen. Its use in the present invention in optional combination with other components, is limited to such compositions and processes that are environmentally friendly, either because the other components are in themselves environmentally friendly or they are used in quantities that do not constitute a danger to individuals or to the environment.

Deteriorative losses of foodstuffs and plant matter during growing, storage and handling is a high priority global problem of considerable social, economic and political importance. Quantitative and qualitative losses during all stages of foodstuff and plant matter growing, storage and handling, impacts first and foremost on the possibility to sustain a reasonable nutritional level and life quality for the earth's inhabitants. Consequently, processes and compositions that can contribute significantly to quantitative and qualitative loss prevention, are of paramount importance. The present invention concerns effective processes and compositions for such purposes. What is more, the present invention concerns environmentally friendly and energy conserving processes and compositions for such ends.

The process and compositions of the invention inhibits plant matter, such as potatoes, seeds and foodstuffs from sprouting, rooting and pathogenic attack and decay, so that such material can be stored under conditions of high relative humidity (70–99+%), optimized to prevent weight loss by dehydration, during storage, for even extended periods of time. The process and compositions of the invention also allow storage under conditions of relatively high temperatures, i.e., low degree of refrigeration, in combination with high relative humidity. This facilitates significant energy savings relative to lower temperature refrigeration, usually required for foodstuff and plant matter storage, particularly under conditions of high relative humidity.

These factors are of prime importance in the post harvest period. But they are also significant in all stages of foodstuff and plant matter growing, storage and handling.

In the event of extended storage period, it can be advantageous to treat the stored plant matter or foodstuff every few weeks with the inhibiting solution and according to the process of the invention. In addition, in the interim period between such treatments, the stored plant matter or foodstuff can be maintained in an aseptic environment by providing a lower level dosage on a more frequent or regular basis, by solutions and treatments that provide the aseptic environment in conjunction with the additional humidity. The process of the invention is readily adaptable to be implemented during transit of the treated matter. This is of considerable significance, since agricultural products, particularly food products, are produced by and large, only during limited seasons of the year. In order for such food products to be available for human and animal consumption during all or at least extended seasons of the year, they must be stored under conditions that minimize losses by dehydration, pathogenic decay, sprouting, rooting and the like, while maintaining organoleptic qualities and preventing other processes that adversely affect their quality.

It is also of the utmost importance that methods and materials employed in extending the effective storage lifetime of perishable foodstuffs and plant matter, should not be detrimental to the consumers' personal health and welfare, nor cause any harm to the environment While one specific application of the present invention so far, has been to extend the effective storage quality and lifetime of potatoes, it is self evident that the same or similar processes and materials can be used to extend the effective storage quality and lifetime, increase crop yields and specifically increase crop yields on a commercial scale, of plant material and foodstuffs in general. This applies not only to similar vegetable food crops, such as, sweet potatoes, carrots, onions, radishes, garlic, etc., but the process and compositions of the invention can be used to good advantage to extend the storage quality and lifetime of potato seeds, sweet potato propagation material, as well as bulbs, including flower bulbs and tubers. The present invention can also be suited to inhibit sprouting in seeds and rains. Furthermore, the process of the invention imparts extended shelf life stability, to all sorts of foodstuff and plant material, including fruits and vegetables, so treated.

A reference that deals at length with the specific topic of potatoes as an example, and some of its related problems is; Smith, O., POTATOES: Production, Storing, Processing, The Avi Publishing Co., Inc., Westport, Conn.

The current total global yield of potatoes is estimated to be in the vicinity of 300 million tons per annun. It is both a basic food staple, because of its inherent nutritional value, being rich in carbohydrates and other nutrients and at the same time is frequently prepared for quick snacks as French fries or chips. It is even used in gourmet dishes, wherein product quality, taste and texture are more critical. Since the conditions under which potatoes grow, prevail only in certain seasons of the year in the various regions of the globe in which they are grown, the issue of preventing qualitative and quantitative losses during storage or during inter regional trade, is vital to those involved with potato growing, storage, trade and consumption. Dehydration during storage is one of the major reasons for weight loss in absolute quantitative terms. At the same time, it contributes to qualitative deterioration in the potatoes themselves. The amount of weight lost by dehydration, during storage is determined by the characteristics of the specific potato varieties involved and by the storage regime. An environment with high relative humidity, prevents water loss by evaporation from stored potatoes. Whereas an environment with low relative humidity can take up a substantial amount of moisture from stored potatoes. Water loss by dehydration of stored potatoes is weight loss of the stored product and consequently a direct economic loss.

Moreover, water losses from stored potatoes cam adversely affect their quality in other ways. Tubers that have lost significant quantities of water by dehydration, are softer than tubers that have been stored under conditions that reduce or prevent such water losses. They are also more subject to bruising and consequently more vulnerable to pathogenic attack and decay.

To prevent weight loss due to dehydration, potatoes are normally stored under conditions of high relative humidity. Such conditions, unless certain counter measures are invoked, are known to promote sprouting and rooting of the stored potatoes, undesirable processes that contribute to the deterioration in potato quality and sometimes even total loss of the potatoes. In addition, high humidity environment frequently favors the growth of pathogens that both contribute to and promote qualitative and quantitative losses.

The materials in use up to now to prevent such undesirable consequences of storage include, isopropylphenylcarbarnate (IPC), chloro isopropylphenylcarbarnate (CIPC) (see for example, Hajslova, J., and Davidek, J., 1986, Sprout inhibitors IPC and CIPC in treated potatoes, Nahrung Food, 30, 75–79), maleic hydrazide (see for example, Yada, R. Y., Coffin, R. H., Keenan, M. K, Fitts, M, Duffault, C. and Tai G. C. C., 1991, Effect of maleic hydrazide on potato yield, sugar content and chip color etc., Amer. Potato J., 68, 705–709), 1,2-dihydro-3,6-pyridazinedione and 2,3,5,6-tetrachloronitrobenzene (TCNB).

Use of CIPC is the most widespread practical method today of keeping potatoes sprout free during storage. However, the use of this sprout inhibitor creates a number of problems. These include, suppression of suberization and periderm formation, requiring as a consequence special additional treatment after the curing process. Moreover, CIPC leaves toxic residues on the tubers to which it is applied. The ambient storage temperature required to inhibit sprouting during potato storage is 2–4° C. Maintaining this relatively low temperature requires significant energy expenditure and cost. There is also a tendency for starches to be converted to sugars at temperatures below 9° C. and thereby degrade the taste characteristics of the potatoes, particularly potatoes intended for industry. Such potatoes suffer therefore from lower consumer acceptability, while for some industrial application, such potatoes are totally unacceptable. Moreover, CIPC has to be volatilized at relatively high temperatures (170–180° C.) before introduction into the storage chamber, thereby effecting an undesirable burden on the refrigeration system and an extra expenditure of energy.

For potatoes harvested during the normal potato harvest season, two options are available to prevent sprouting and rooting. One involves maintaining storage temperatures between 2–4° C. The other allows storage at higher temperatures, but requires treatment with CIPC and other chemicals that inhibit sprouting. In the case of late harvest potatoes, storage at temperatures even as low as 2–4° C., does not provide assurance of effective sprouting inhibition. In such cases, even supplemental treatment with CIPC, does not assure effective sprouting inhibition. On the other hand, the process of the present invention, does provide effective sprouting and rooting inhibition over a wide temperature range.

While the usual storage temperatures employed with CIPC treatment are within the range 7–8° C., the process of the invention has been found to impart effective sprouting and rooting inhibition over a wide range of temperatures. This includes the current relevant range of storage from 2–10° C. It also includes a wide range of ambient temperatures. It should be emphasized once more, that the possibility of allowing higher storage temperature, provides a way of achieving substantial energy savings with economic, qualitative, quantitative and ecological benefits. Furthermore, certain embodiments of the present invention facilitate adjustment of the carbon dioxide-oxygen gas balance in the storage rooms, thus preventing "black-heart" deterioration in the stored potatoes. CIPC and similar based treatment processes do not inherently involve such gas balance adjustments.

It should be pointed out that CIPC is not effective at temperatures of 5° C. and below. In various circumstances, such as late harvest, sprouting can occur at such temperatures. However, the process and compositions of the preset invention, is effective in inhibiting sprouting, even at temperatures of 5° C. and below. Experiments have shown that the interval between successive treatments for effective control by the process and compositions of the present invention, can be prolonged to as long as two to six months, under these conditions. The wide temperature range that is suitable for storing plant matter and foodstuffs treated by the process and compositions of the present invention, also provides greater flexibility to accommodate a relatively wide variety of different conditions encountered in various facilities and environments. The process of the invention can also be implemented while the plant matter or foodstuff is being transported, thus providing a means for inhibiting deteriorative processes in transit, but also conserving time.

CIPC has a number of additional deficiencies that the process of the present invention overcomes. CIPC is systemic to tubers, fruits and food stuffs treated with it. That is to say it penetrates into the bulk of such tubers, fruits and food stuffs. As a consequence, this results in a number of limitations, that include;

(1) regulations that prohibit use of CIPC, to treat certain food materials;

(2) potatoes and similar foodstuffs that been treated with CIPC must undergo a waiting period of at least a month or two before they are marketed, in order to allow the CIPC to decompose;

(3) a storage room or bin in which CIPC treatment took place, is prohibited from being used for food or seed storage;

(4) application of CIPC requires special equipment that is expensive to acquire and maintain, a high and specific temperature to transform the liquid into a gas, and constant supervision of a skilled technician during the entire period of operation;

(5) CIPC attacks plastic, leaves a black, difficult to remove, layer on the surface of the storage room and leaves active residues in the walls for a period of years.

(6) CIPC has to be volatilized at high temperatures before introduction into storage chambers, thereby adversely affecting the temperature balance therein.

All the above mentioned disadvantages of CIPC are eliminated when the process of the present invention is used instead of CIPC treatment. This is because the decomposition products of the compounds used in the present invention are harmless. For the most part, they consist of water and oxygen, with merely trace, practically undetectable quantities of other optional components, when used. In certain embodiments, it also provides for carbon dioxide-oxygen gas balance adjustment, thereby inhibiting "black-heart" deterioration of stored potatoes.

Finally, in certain countries the use of CIPC is either restricted or in the process of being restricted and even prohibited. The other materials mentioned above aside from those of the present invention, do not constitute attractive alternatives to the use of CIPC, because of similar or other deficiencies.

Hydrogen peroxide is a well known non-polluting oxidizing agent. A comprehensive article summarizing its production, uses and other features is presented in Kirk-Othmer, Encyclopedia of Chemical Technology-4th Edition, Vol. 13, pp. 961–995. The said article and its bibliography are included herein by reference. The known uses for hydrogen peroxide described in the Kirk-Othmer article include water treatment, disinfection and sterilization of contact surfaces of food packaging. The use of hydrogen peroxide for space decontamination, was also indicated as holding promise. The bibliography also cites various patents that involve stabilized hydrogen peroxide compositions. Such a composition containing silver salt or complex is described in WO 96/18301, while U.S. Pat. No. 4,915,955 concerns a stabilized silver salt compound or colloid for mixing with hydrogen peroxide to produce effective disinfectants. No mention is made in the article concerning the use of hydrogen peroxide or its compositions for treating foodstuffs or plant material.

The use of hydrogen peroxide in combination with silver ions for disinfection of water is also described in Shuval, H., et al, Water SCi. Technol., (1995), 31(5–6, Health-Related Water Microbiology 1994), 123–9 and in Shuval E, et al, Water Supply, (1995), 13(2 IWSA International Specialized Conference on Disinfection of Potable Water, 1994), 241–51.

While occasional and sporadic reports in technical and sales promotional literature and meetings have indicated that hydrogen peroxide treatment can be beneficial for foodstuff and plant matter conservation, a recent summary presented at a meeting of the European Association for Potato Research that took place on Mar. 25–29, 1998, at Aberdeen, Scotland, indicated that such treatments are less effective than available alternatives. See, for example, Clayton, R. C., and Black, S., POTATO SEED STORE HYGIENE: CLEANING, DISINFECTION OR BOTH? Presentation at meeting of European Association for Potato Research, Mar. 25–29, 1998, at Aberdeen, Scotland.

Among publications that one might note as indicating possible benefits from hydrogen peroxide treatment of foodstuffs and plant matter, one can cite the following:

Afek, A., et al, NEW APPROACHES FOR INHIBITION OF SPROUTING AND REDUCTION OF WEIGHT LOSS DURING POTATO STORAGE, Abstracts of Conference Papers, Posters and Demonstrations, 13th Triennial Conference of the European Association for Potato Research, Jul. 14–19, Veldhoven Netherlands and Postharvest, Taupo, New Zealand, August, 1996. This publication describes an ultra-sonic technique for treating potatoes in storage with a solution containing 25% ethanol and 0.3% of a commercial concentrate containing hydrogen peroxide and silver ion. While the efficiency of the treatment in sprout inhibition was reported to be comparable to the standard CIPC treatment, no indication was given of effectiveness of treatment with aqueous hydrogen peroxide without the ethanol.

A sales promotion brochure for a preparation with the name Virosil-Agro, claims that the preparation is effective in preventing post-harvest deterioration in a large variety of fruits and vegetables. The preparation itself is described as "a multicomponent complex formulation containing hydrogen peroxide and silver in cationic form." The forms of application do not include "Dry Fog".

In an article in Hebrew by Nir, A. and Heller, D., in HaSadeh, Vol. 74, No. 12, pp. 1326–7, mixed results are reported for the disinfection of hatching eggs with a hydrogen peroxide preparation applied with an ultra-sonic fogger. No explanation is provided for the lack of consistency in results, although good results were reported for the more recent series of tests.

The mixed and inconclusive results observed so far for application of preparations containing hydrogen peroxide to foodstuffs and plants can probably be rationalized as follows:

Hydrogen peroxide is a strong oxidizing agent. It is also a strong disinfectant, effectively eliminating or at least reducing a wide variety of pathogens, including pathogens that cause decay. Being however at the same time a strong oxidizing agent, it can also cause damage surface tissues and protective peels and coatings of foodstuff and plant matter, thereby making them more vulnerable to pathogen penetration. Consequently, reluctance so far to adopt environmentally friendly, hydrogen peroxide based processes and compositions for treating foodstuffs and plant matter to prevent qualitative and quantitative losses during storage and handling, can be attributed to a large extent to the absence of reliable processes and compositions for this purpose, that provide consistently effective results.

Consequently, it is an object of certain aspects of the present invention to provide a process and/or hydrogen peroxide containing compositions that allows plant matter and foodstuffs to be stored under conditions of high relative humidity and high relative temperature, while inhibiting detrimental processes that cause deterioration in quality that are frequently promoted by conditions of high relative humidity and temperature. Thus it is possible to gain the various benefits of high humidity and temperature storage without incurring detrimental consequences, frequently effected by storage of foodstuffs in a high humidity and high relative temperature ambiance. The sprouting, rooting and "black-heart" formation of potatoes or similar tubers during storage, can be cited as examples of detrimental processes that occurs during storage, particularly in a high humidity and high relative temperature ambiance.

Its is also an object of certain aspects of the present invention to provide a treatment process and/or compositions that prevent sprouting, rooting and "black-heart" formation of potatoes, other tubers, bulbs, seeds, grains, onions and other food and plant propagation material, particularly under conditions of high humidity and relatively high temperature storage. The said process also allows for convenient adjustment of carbon dioxide-oxygen gas balance, thereby inhibiting "black-heart" deterioration in potatoes.

It is also an object of certain aspects of the present invention to provide a process and/or compositions that result in energy savings during storage and handling of foodstuffs and plant matter.

It is also an object of certain aspects of the process of the present invention to apply a treatment process and/or compositions on seeds and plant propagation material that reduce losses from harvest until sowing, inhibit sprouting, protect seeds without loss of water necessary for growth, allow seeds to be maintained in an aseptic condition, so that they do not transmit infections and diseases, from country to country, to neighboring seeds, to the harvests they will produce or the earth in which they are planted.

It is another object of certain aspects of the present invention to provide processes and/or compositions that effect and promote Epical Dominance Breakdown, thereby inhibiting premature undesirable sprouting, but ultimately promoting enhanced sprouting capability, and in addition promoting and enhancing part of or all the following benefits and advantages, in appropriate plant matter, e.g. in potatoes (1) More stems per tuber relative to an untreated control;
(2) greener and richer foliage;
(3) more uniform growth height;
(4) more tubers per maternal tuber;
(5) higher yields in kg/square meter;
(6) greater uniformity in the size distribution of the harvest product, particularly in standard sizes for industry, for marketing and for seeds;
(7) the pre-treatment in accordance with process and compositions of the invention preserves the maternal tuber from deteriorative processes that would ultimately contaminate the yields and
(8) because the effects of the treatment on seeds is beneficial, total flexibility is provided to the storers of potatoes, to market his produce to industry or/and consumer markets and/or for seed, all in accordance with market conditions. This can be done immediately after treatment, without having to wait a month, as required after treatment with CIPC.

The treatment process and/or compositions provided by the invention are total substitutes to the treatment and compositions in use at present for seed matter before export and/or before actual sowing. Furthermore, it is friendly to man and the environment, simple and economical to implement, The most common material in use until recently and still in use in some countries for this purpose, is ethyl methyl mercury chloride. This material contains a high concentration of organic mercury and has therefore been prohibited for use in most of the counties of the world. This is because it is dangerous to the health of the user, and contains a toxic metal that contaminates the ground and aquifers.

The new treatment process and/or compositions of the present invention are more efficient. They possess additional beneficial and superior properties. They are friendly to the user and the environment, in comparison to other alternative seed treatments with various sorts of fungicides and fumigation with formaldehyde.

It is an additional object of certain aspects of the present invention to provide a process and/or compositions for preventing modes of qualitative and/or quantitative losses of potatoes during storage, for example, by decay caused by infection with microorganisms, fungi, algae, yeasts, molds and viruses.

It is yet another purpose of certain aspects of the present invention to provide storage process for storage of plant matter and foodstuffs that prevents qualitative and quantitative losses during storage, by undesirable microbiological or biochemical processes of the foodstuff itself, including when such processes effected and/or promoted by high humidity and high temperature storage conditions.

It is also an object of certain aspects of the present invention to provide processes and compositions that can be used to reduce and eliminate harmful organisms and substances from earth, equipment, materials, spaces and surfaces.

Moreover, it is an important object of certain aspects of the present invention to achieve the above purposes in a simple way, that is safe to use, non-toxic, odorless, without hazardous residues and/or side effects, compatible with the environment and that does not leave any undesirable chemical residues in the materials or water, earth, other growth media and substrates, or on equipment, materials, water, spaces and surfaces exposed to the treatment by the process and compositions of the present invention, or endanger the heath of operators implementing the process or handling the compositions or the foodstuffs treated by them. The process and compositions of the present invention are cost effective.

SUMMARY OF THE INVENTION

Percentages throughout the specification indicate weight by weight percentages.

In accordance with a preferred embodiment of the present invention, there is provided an environmentally compatible process for treating plant matter and foodstuffs, during storage, distribution and marketing, preplanting, growing, and pre and/or post harvest, to increase yields, eliminate health hazards, impart storage stability, extend shelf life and inhibit premature sprouting, rooting, germination, blossoming, decay, "black-heart" formation, pathogenic losses and other processes causing losses in quality and/or quantity of said plant matter and foodstuffs, said plant matter and foodstuffs including tubers—such as potatoes, bulbs, seeds grains and other germinating matter or items, plant vegetative propagation matter or items, as well as various fruits and vegetables including solanaceous fruits and vegetables, by treating the said plant matter or foodstuffs, during storage and/or distribution and marketing, preplanting and/or during pre and/or post harvest with an effective aqueous dosage comprising an effective concentration of hydrogen peroxide and optionally comprising an effective dosage of one or more additional components selected from the following types of substances:

(i) effective trace concentrations of dispersed metals or metal ions;
(ii) effective concentrations of other and/or additional hydrogen peroxide activators, synergists and promoters;
(iii) effective concentrations of hydrogen peroxide stabilizers and modifiers;
(iv) effective concentrations of pH regulators;
(v) effective concentrations of organic and/or inorganic additives, wherein the effective concentration of hydrogen peroxide, time of treatment and form of application are such as to prevent such plant matter and foodstuffs quality and/or quantity loss, but at the same time not so high as to cause or induce damage to the plant matter and foodstuffs themselves.

In accordance with another preferred embodiment of the present invention, there is provided a process for preventing premature sprouting and enhancing the productivity in plant growth material, e.g., potatoes, potato tubers, potato growth material or other plant growth material, by effecting Epical Dominance Breakdown in the said potatoes, potato tubers, potato growth material or other plant growth material, comprising treating the potatoes, potato tubers, potato growth material or other plant growth material with an effective aqueous dosage comprising an effective concentration of hydrogen peroxide and optionally comprising, one or more additional components selected from the following types of substances:
- (i) effective trace concentrations of dispersed metals or metal ions;
- (ii) effective concentrations of other and/or additional hydrogen peroxide activators) synergists and promoters;
- (iii) effective concentrations of hydrogen peroxide stabilizers and modifiers;
- (iv) effective concentrations of pH regulators;
- (v) effective concentrations of organic and/or inorganic additives.

In accordance with another preferred embodiment of the present invention, there is provided a composition for treating in an environmental friendly manner, plant matter and foodstuffs, during storage distribution and marketing, preplanting, growing, and pre and/or post harvest, to increase yields, eliminate health hazards, impart storage stability, extend shelf life and inhibit premature sprouting, rooting, "black-heart" formation, germination, blossoming, decay, pathogenic losses and other processes causing losses in quality and/or quantity of said plant matter and foodstuffs, and promote epical dominance breakdown, said plant matter and foodstuffs including tubers—such as potatoes, bulbs, seeds grains and other germinating matter or items, plant vegetative propagation matter or items, as well as various fruits and vegetables including solanaceous fruits and vegetables, said composition being also suitable to treat earth, other growth media and substrates, equipment materials, water, spaces and surfaces to reduce and eliminate harmful organisms and substances therefrom, comprising
- (a) 0.001% to 50% of hydrogen peroxide
- (c) 0.001% to 5% of metal ion selected from the group consisting of copper, zinc, nickel, iron, manganese, molybdenum, potassium or combinations thereof and optionally
- (i) effective trace concentrations of other dispersed metals or metal ions;
- (ii) effective concentrations of other and/or additional hydrogen peroxide activators, synergists and promoters;
- (iii) effective concentrations of hydrogen peroxide stabilizers and modifiers;
- (iv) effective concentrations of pH regulators;
- (v) effective concentrations of organic and/or inorganic additives.

In accordance with yet another preferred embodiment of the present invention, there is provided a composition for treating in an environmental friendly manner, plant matter and foodstuffs, during storage, distribution and marketing, preplanting, growing, and pre and/or post harvest to increase yields, eliminate health hazards, impart storage stability, extend shelf life and inhibit premature sprouting, rooting ""black-heart"-heart" formation, germination, blossoming, decay, pathogenic losses and other processes causing losses in quality and/or quantity of said plant matter and foodstuffs, and promote epical dominance breakdown, said plant matter and foodstuffs including tubers—such as potatoes, bulbs, seeds grains and other germinating matter or items, plant vegetative propagation matter or items, as well as various fruits and vegetables including solanaceous fruits and vegetables, said composition being also suitable to treat earth, other growth media and substrates, equipment, materials, water, spaces and surfaces to reduce and eliminate harmful organisms and substances therefrom, comprising
- (a) 0.001% to 50% of hydrogen peroxide
- (b) 0.001% to 2.5% of silver ion
- (c) 0.001% to 2.5% of metal ion selected from the group consisting of copper, zinc, nickel, iron, manganese, molybdenum, potassium or combinations thereof and optionally
- (i) effective trace concentrations of other dispersed metals or metal ions;
- (ii) effective concentrations of other and/or additional hydrogen peroxide activators, synergists and promoters;
- (iii) effective concentrations of hydrogen peroxide stabilizers and modifiers;
- (iv) effective concentrations of pH regulators;
- (v) effective concentrations of organic and/or inorganic additives.

In yet another embodiment of the invention, there is provided an environmentally compatible process for reducing and eliminating harmful organisms and substances from earth, equipment, materials, water, spaces and surfaces by treating the said earth, other growth media and substrates, equipment, materials, water, spaces and surfaces with an effective dosage of a composition comprising an effective concentration of hydrogen peroxide and optionally comprising, an effective dosage of one or more additional components selected from the following types of substances:
- (i) effective trace concentrations of dispersed metals or metal ions;
- (ii) effective concentrations of other and/or additional hydrogen peroxide activators, synergists and promoters;
- (iii) effective concentrations of hydrogen peroxide stabilizers and modifiers;
- (iv) effective concentrations of pH regulators;
- (v) effective concentrations of organic and/or inorganic additives,

DETAILED DESCRIPTION OF THE INVENTION

The preferred range of concentrations or hydrogen peroxide for use in intermittent treatment of foodstuff and plant matter in accordance with the process of the present invention is from 0.001% to 50%, preferably from 0.01% to 20% and more specifically from 0.1% to 15%. The preferred range of concentrations for continuous or short interval treatment is 10 PPM to 40%.

The range of concentrations of dispersed metal and/or metal ion for use in accordance with this invention is from 1 PPB to 5%, preferably from 10 PPB to 10,000 PPM, more specifically from 20 PPB to 2000 PPM and even more specifically from 20 PPB to 1000 PPM. The combination of hydrogen peroxide with appropriate metal ion(s) provides in certain instances a synergistic effect by which the hydrogen peroxide effect is enhanced. In addition, the minute trace residue quantities of the metal ion(s) have been found to have a slower but longer lasting beneficial effect on the prevention of quality and quantity deterioration of foodstuff and plant matter.

The treatment of the treated matter in accordance with this invention can be implemented satisfactorily in various ways. These include, in certain cases dipping the treated matter in the above mentioned solution(s) or spraying the solution(s) onto the treated foodstuff or plant matter. However it should be pointed out that water or condensed water droplets on the surface of foodstuff and plant matter can enhance the proliferation of pathogens and thus have a detrimental effect. This is of particularly concern when it is important to maintain storage conditions of high relative humidity, such as in the storage of potatoes, to prevent material loss due to evaporation and other forms of deterioration induced by a low humidity environment.

Intermittent treatment by means of the process and compositions of the present invention, protects foodstuff and plant matter so treated form adverse effects of condensation of water on the surfaces of the foodstuffs and matter, so treated.

The application of the solution in the form of ultra small drops by solution atomizing systems that produce "dry" fogs with particles sizes of less than and up to 1000 microns in diameter, has been found to provide particularly beneficial results. These include compensation for or prevention of water loss, inhibition of spouting, rot inhibition, less overall losses and higher yields for treated seeds. The beneficial "dry" fog is attributed to the fact that very small particles behave to a large extent like a gas. They facilitate the achievement of very high relative humidity, i.e., even as high as 99%+, without any condensation on the stored matter. Furthermore, the small particles show a very high penetrability into small cracks and spaces. As a consequence, even when potatoes are stored in ordinary stacks or sacks, the "dry" fog storage has a high degree of penetrability and accessibility to all points in the stack or sack. This means that even in the simplest and most space compact facilities, stored plant matter, such as potatoes and similar items, can be effectively treated to prevent weight loss due to dehydration as well as softening and other deteriorative processes brought about by an inadequate humidity environment.

Another benefit of the "dry" is that it allows higher concentrations of hydrogen peroxide and other active ingredients to be used without causing damage to the protective peel or surface of the plant matter so treated. The higher concentration of treating solutions enhances their effectiveness in the rapid elimination of pathogens. When the foodstuff and plant matter is treated by dipping or ordinary spraying, the optimal hydrogen peroxide concentration should be substantially between 0.5%–1.5% and treating time between a few seconds up to a few minutes. When the treatment is applied as a "dry" fog, the hydrogen peroxide concentration may be up to 40% and the time of application from several hours to a number to a number of days.

A further benefit of application by fog is that it allows for convenient adjustment of the carbon dioxide-oxygen balance in the storage room or chamber, thus inhibiting "black heart" deterioration. Preferably, the air to liquid volume ratio in the fog should be between 300:1 and 1200:1, more preferably between 500:1 and 700:1.

In certain aspects and applications, the beneficial effects of the process of the present invention are enhanced by the addition of certain additives to the treatment solution, these additives may include:

Stabilizers and modifiers, such as but not limited to, citric acid, tartaric acid, boric acid, bromic acid, stannates, phosphoric acids etc.

pH Regulators, primarily mineral and organic acids, such as but not limited to phosphoric acid, peracetic acid, hydrochloric acid, sulfuric acid, etc. For optimum effectiveness, the pH should be lower than 6 and preferably between 1–4.

Trace element activators synergists and promoters, such as but not limited to, dispersions of metal, non-metals or ions (of various valences when appropriate) such as, copper, zinc, nickel, iron, potassium, manganese, silver, chromium, molybdenum, magnesium, boron, phosphorus, iodine, sulfur, citrate, etc.

Organic or inorganic additives, such as but not limited to, peracetic acid, phenol, gelatin, glycerin, sodium azide, polymoxin B, sodium bicarbonate, pectin, salicylic acid, etc.

EXAMPLES

Example 1

In several experiments conducted in a storage room containing hundreds of metric tons of potatoes, a hydrogen peroxide-metal ion solution was introduced with a flogger overnight until a relative humidity level of 80–99% was attained. The potatoes were kept in the storage room for 5 months, during which time fogging treatment was effected 10–50% of the time. The result of the spraying was that losses due to disease were reduced from 8% to 2%, while losses due to dehydration were reduced from 5% to 2%. Therefore the total loss reduction was from 13% to 4.5%, a net average reclamation of 8.5%.

Example 2

The effect of treatment with various solutions of aqueous hydrogen peroxide plus additives at the following concentrations: 0% (control) and 0.1–30%, by dipping for various lengths of time. Clear-cut sprout inhibition was obtained for bulbs so treated, compared to the control, as well as decay prevention for extended time.

In certain concentrations, an opposite result was obtained of rot and severe phytotoxic damage to the tubers.

Each of the treatments were repeated five times. Each time involved 50 kilograms of potatoes.

Example 3

Same as Example 2, except that instead of dipping, the solutions were sprayed onto the foodstuff substrate until dripping (high volume).

Example 4

Same as Example 3, except that the spraying onto the foodstuff substrate was low volume.

Example 5

Same as Example 3, except that the spraying onto the foodstuff substrate was ultra low volume.

Example 6

Same as Example 3, except that the spraying onto the foodstuff substrate was by fogging. The gas liquid volume ratio was 600:1.

Examples 7–11

Each of the treatments described in examples 2–6 above were carried out on potato seeds.

Examples 12–16

Each of the treatments described in examples 2–6 above were carried out on wheat seeds, corn (maize), various grains and solanaceous plants. The concentrations of the hydrogen peroxide solutions were varied between 0.1–60%. The species so treated were examined after periods of 7–10 days. In all cases, no sprouting, blossoming and germination were observed The same species were examined after varying periods of several weeks to several months. Inhibition of decay was observed.

In certain concentrations, an opposite result was obtained, of rot and severe phytotoxic damage to the tubers.

Example 17

750 tons of potatoes of the Desiree variety were stored in each of three cold rooms for six months at 10° C. At an average relative humidity of 97% provided as 3–7 micron droplets, weight loss after this time was only 2.8%. With a regular humidifier and average relative humidity of 92%, the weight loss was 6%. The weight loss in the control average humidity 85% was 11%.

In addition, the quality of potatoes stored without providing humidity was low because of softening. The firmness of the different batches of potatoes described above were as follows: 64 newtons for 97% relative humidity; 58 newtons for 92% relative humidity and 48 newtons for 85% relative humidity. Potato firmness before storage was 70 newtons.

Example 18

Experiments were conducted to test the effectiveness of treating potato seeds to prevent sprouting, with a "dry" fog comprising, hydrogen peroxide, silver ion and phosphoric acid. After preliminary treatment with the active solution, the storage conditions were maintained at 90% relative humidity and 10° C. The results were as follows:

| Concentration (PPM) | | Sprouting (%) | | |
| --- | --- | --- | --- | --- |
| $H_2O_2$ | Ag ion | one month | two months | three months |
| 0 | 0 | 15 | 27 | 35 |
| 500 | 1 | 4 | 23 | 31 |
| 1,250 | 2.5 | 0 | 3 | 6 |
| 5,000 | 10 | 0 | 2 | 5 |

By repeating the above dosage on a monthly basis, it was possible to totally eliminate sprouting for extended periods. However at levels above 25% $H_2O_2$, damage was caused to the peel that developed rapidly to rot.

Example 19

Experiments were conducted to test the effectiveness of treating potato seeds to prevent sprouting, with a "dry" fog containing hydrogen peroxide and silver ion. After preliminary treatment with the active solution, the storage conditions were maintained at 90% relative humidity and 10° C. The results were as follows:

| Concentration (PPM) | | | Sprouting (%) | | |
| --- | --- | --- | --- | --- | --- |
| $H_2O_2$ | Ag ion | Cu Ion | one month | two months | three months |
| 0 | 0 | 0 | 15 | 27 | 35 |
| 500 | 0 | 0 | 8 | 22 | 32 |
| 500 | 1 | 0 | 4 | 23 | 31 |
| 500 | 0 | 1 | 6 | 17 | 27 |
| 500 | 0.1 | 0.9 | 2 | 13 | 18 |

By repeating the above dosage on a monthly basis, it was possible to totally eliminate sprouting for extended periods. However at levels above 25% $H_2O_2$, damage was caused to the peel that developed rapidly to rot.

Example 20

Experiments were conducted to test hie effect on yield enhancement of treating potato seeds with solutions containing hydrogen peroxide and silver ion. The potato seeds were initially harvested in late June and put into cold storage at 9–10° C. and 96–99+% RH, initially untreated. Approximately one month later, each batch of various potato seed varieties was treated with a dose of a solution containing hydrogen peroxide and silver ion, the ratio of the active ingredients to the potato seeds being 2–5% $H_2O_2$ and 40–100 PPM Ag ion on a wt/wt basis. Each batch was treated three more times. The second treatment took place about three and one half weeks after the first treatment and was at the same dosage level. The third treatment was almost four weeks after the second treatment, but the dosage level was reduced by half. The fourth treatment was about three weeks later also at the half dosage level.

The average potato yields in kilogram/square-meter for various potato seed varieties, were as follows:

| | Treated Potatoes | Untreated Potatoes |
| --- | --- | --- |
| After 84 days | 2.28 kg/m$^2$ | 1.65 kg/m$^2$ |
| After 94 days | 2.56 kg/m$^2$ | 2.04 kg/m$^2$ |

In addition to the higher yields in weight per unit area, the potatoes that were produced from treated potato seeds had a more uniform size distribution as well as a higher yield of marketable sizes relative to those of the untreated control. In addition, the maternal tubers remained robust and did not deteriorate so that the crop was not contaminated. The problem of maternal tuber deterioration and crop contamination is a basic problem of untreated potato seeds.

General Examples

The following is a number of additional examples of applications of the present new invention in various areas requiring humid and aseptic conditions:

(1) Treatment of hot-house plants and growth products;
(2) Treatment related to growing and marketing of mushrooms and buds;
(3) Treatment in meat storage;
(4) Treatment of eggs for eating or incubation for increasing moisture and preventing infection;
(5) Treatment of incubation spaces, incubation cells and hatching cells.
(6) Treatment of space and equipment in surgical operation rooms;
(7) Treatment of space and equipment in crowded halls and enclosed areas, such as, subway stations, buses, airplanes, ships and the like;
(8) Various treatments of sown earth to prevent ground pollution, instead of methyl bromide whose use is being prohibited.
(9) Storage spaces, greenhouses, hen houses, etc.

While certain embodiments of the invention have been hereinbefore particularly described, it will be apparent to anyone skilled in the art that many modifications and variations may be made, that do not deviate from the main features or spirit of the invention. The invention is accordingly not to be construed as restricted to such embodiments, but rather to its concept, spirit and general scope.

What is claimed is:

1. A method of treating potatoes during storage, comprising contacting said potatoes with a hydrogen peroxide solution, and inhibiting sprouting of said potatoes, the improvement wherein:

said hydrogen peroxide solution is at a maximum pH of 6; contains metallic ions of at least one of silver, copper and zinc, said metallic ions being present in an amount of 10 ppb to 20,000 ppm; and contains at least one of peracetic, nitric, sulfuric and phosphoric acid;

said solution is applied in the form of a dry fog, fumes or smoke, wherein said solution comprises microdroplets having a particle size of 0.001 to 100 microns, said potatoes are maintained at a high relative humidity during storage, and sprouting of said potatoes is inhibited.

2. The method of claim 1 wherein said pH is no greater than 4.

3. The method of claim 2 wherein said metallic ions comprises silver ion in an amount of 50 ppb to 10,000 ppm.

4. The method of claim 3 wherein said microdroplets have a maximum particle size of 30 microns.

5. The method of claim 3 wherein said acid comprises phosphoric acid.

6. The method of claim 5 wherein said microdroplets have a maximum particle size of 10 microns.

7. The method of claim 6 wherein said treating comprises fogging, and said fogging comprises an air to liquid volume ratio of between 300:1 and 1200:1.

8. The method of claim 7 wherein said fogging comprises an air to liquid volume ratio of between 500:1 and 700:1.

9. The method of claim 1 wherein the concentration of hydrogen peroxide in said hydrogen peroxide solution is 0.1–15%.

10. The method of claim 1 wherein said potatoes are stored for at least five months, and said treatment is repeated intermittently during said storage, intervals between said treatments being approximately 3 or 4 weeks.

11. The method of claim 10 wherein said potatoes are maintained at a temperature of at least 10° C. during storage.

12. The method of claim 1 wherein said potatoes are stored for at least three months, and said treatment is repeated intermittently during said storage, intervals between said treatments being approximately three or four weeks.

13. The method of claim 12 wherein said potatoes are maintained at a temperature of at least 10° C. during storage.

14. The method of claim 1 wherein said potatoes are stored for at least three months, and said treatment is repeated intermittently 10–50% of the time during said storage.

15. The method of claim 1, wherein said potatoes are stored for at least five months, and said treatment is repeated intermittently 10–50% of the time during said storage.

16. The method of claim 1, wherein said potatoes are stored for at least five months, and said treatment is carried out substantially continuously during said storage.

17. The method of claim 16 wherein said potatoes are maintained at a temperature of at least 10° C. during said storage.

18. The method of claim 1, wherein said treatment further comprises inhibiting rooting of said potatoes.

19. The method of claim 1, wherein said potatoes are seed potatoes, and said treatment comprises breaking epical dominance in said seed potatoes.

* * * * *